US008623377B2

(12) United States Patent
Moudgil et al.

(10) Patent No.: US 8,623,377 B2
(45) Date of Patent: Jan. 7, 2014

(54) JOINT-HOMING PEPTIDES AND USES THEREOF

(75) Inventors: Kamal Moudgil, Silver Springs, MD (US); Ying-hua Yang, Timonium, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 13/537,537

(22) Filed: Jun. 29, 2012

(65) Prior Publication Data

US 2013/0004415 A1 Jan. 3, 2013

Related U.S. Application Data

(60) Provisional application No. 61/502,376, filed on Jun. 29, 2011.

(51) Int. Cl.
*A61K 39/00* (2006.01)
(52) U.S. Cl.
CPC ..................................... *A61K 39/00* (2013.01)
USPC ........................................ 424/192.1; 530/350
(58) Field of Classification Search
None
See application file for complete search history.

(56) References Cited

U.S. PATENT DOCUMENTS

2005/0100555 A1* 5/2005 Pitzalis et al. ............. 424/192.1

OTHER PUBLICATIONS

Szekanecz, Angiogenesis and its targeting in rheumatoid arthritis, journal, 2009, p1-7, vol. 51, Vascul Phamacol, US.
Storgard, Decreased angiogenesis and arthritic disease in rabbits treated with an avb3 antagonist, journal, 1999, p47-54, vol. 103, J clin Invest, US.
Gerlag, Suppression of murine collagen-induced arthritis by targeted apoptosis of synovial neovasculature, journal, 2001, p357-361, vol. 3, Arthritis Res, US.
Whitney, Fluorescent peptides highlight peripheral nerves during surgery in mice, Manuscript, 2011, p352-356, vol. 29, Nat Biotechnol, US.
Essler, Molecular specialization of breast vasculature: A breast-homing phage-displayed peptide binds to aminopeptidase P in breast vasculature, journal, 2002, p2252-2257, vol. 99, Proc Natl Acad Sci USA, US.
Arap, Cancer Treatment by Targeted Drug Delivery to Tumor Vasculature in a Mouse Model, journal, 1998, p377-380, vol. 279, Science, US.
Askoxylakis, A New Peptide Ligand for Targeting Human Carbonic Anhydrase IX, Identified through the Phage Display Technology, journal, 2010, p. e15962, vol. 5, PLos ONE, US.
Deutscher, In-labeled KCCYSL peptide as an imaging probe for ErbB-2- expressing ovarian carcinomas, manuscript, 2009, p583-590, vol. 52, J Labelled Comp Radiopharm, US.

Koivunen, Isolation of a Highly Specific Ligand for the as/3t Integrin from a Phage Display Library, journal, 1994, p373-380, vol. 124, J Cell Biol, US.
Sugahara, Tissue-penetrating delivery of compounds and nanoparticles into tumors, manuscript, 2009, p510-520, vol. 16, Cancer Cell, US.
Zhou, Synergistic effect of antiangiogenic nanotherapy combined with methotrexate in the treatment of experimental inflammatory arthritis, manuscript, 2010, p1065-1074, vol. 5, Nanomed, US.
Pasqualini, Aminopeptidase N Is a Receptor for Tumor-homing Peptides and a Target for Inhibiting Angiogenesisa, journal, 2000, p722-727, vol. 60, Cancer Res, US.
Chang, Antiangiogenic Targeting Liposomes Increase Therapeutic Efficacy for Solid Tumors, journal, 2009, p12905-12916, vol. 284, J Biol Chem, US.
Lee, Identification of Synovium-Specific Homing Peptides by in Vivo Phage Display Selection, journal, 2002, p2109-2120, vol. 46, Arthrutus Rheum, US.
Koning, Targeting of Angiogenic Endothelial Cells at Sites of Inflammation by Dexamethasone Phosphate-Containing RGD Peptide Liposomes Inhibits Experimental Arthritis, journal, 2006, p1198-1208, vol. 54, Arthritis Rheum, US.
Wahl, Synthetic Fibronectin Peptides Suppress Arthritis in Rats by Interrupting Leukocyte Adhesion and Recruitment, journal, 1994, p655-662, vol. 94, J Clin Invest, US.
Halloran, Ley/H: An Endothelial-Selective, Cytokine-Inducible, Angiogenic Mediator, journal, 2000, p4868-4766, vol. 164, J Immunol, US.
Van Belle, Type 1 Diabetes: Etiology, Immunology, and Therapeutic Strategies, journal, 2011, p79-118, vol. 91, Physiol Rev, US.
Rajaiah, Interleukin-27 and Interferon- Are Involved in Regulation of Autoimmune Arthritis, journal, 2011, p2817-2825, vol. 286, J Biol Chem, US.
Maeshima, Two RGD-independent avb3 Integrin Binding Sites on Tumstatin Regulate Distinct Anti-tumor Properties, journal, 2000, p23745-23750, vol. 275, J Biol Chem, US.
Binstadt, Two RGD-independent avb3 Integrin Binding Sites on Tumstatin Regulate Distinct Anti-tumor Properties, journal, 2006, p284-292, vol. 7, Nat Immunol, US.
Brown, Peptidic Tumor Targeting Agents: The Road from Phage Display Peptide Selections to Clinical Applications, journal, 2010, p1040-1054, vol. 16, Curr Pharm Des, US.
Caturegli, Autoimmune thyroid diseases, journal, 2007, p44-48, vol. 19, Curr Opin Rheumatol, US.
Chen, Molecular signatures of disease brain endothelia provide new sites for CNS-directed enzyme therapy, journal, 2009, p1215-1218, vol. 125. Nat Med, US.
Corrigall, Autoantigens and Immune Pathways in Rheumatoid Arthritis, journal, 2002, p281-293, vol. 22, Crit Rev Immunol, US.
David, Role of Major Histocompatibility Complex Genes in Murine Collagen-Induced Arthritis: A Model for Human Rheumatoid Arthritis, journal, 2004, p180-187, vol. 327, Amer J of Medical Sciences, US.

(Continued)

*Primary Examiner* — Jean C. Witz
*Assistant Examiner* — Mindy Newman
(74) *Attorney, Agent, or Firm* — Benjamin Aaron Adler

(57) ABSTRACT

The present invention provides peptides that home to a joint of an animal, wherein said peptide comprises an amino acid motif selected from the group consisting of NQR and ADK. Also provided are methods of treating a subject having an arthritic joint, comprising the step of administering to said subject a pharmacologically effective dose of a composition provided herein.

17 Claims, 11 Drawing Sheets

(56) References Cited

OTHER PUBLICATIONS

Gordon, Multiple Novel Classes of April-specific Receptor-blocking Peptides Isolated by Phage Display, journal, 2010, p166-177, vol. 396, J of Molecular Biology, US.

Gorman, Immune-mediated pathways in chronic inflammatory arthritis, journal, 2008, p221-238, vol. 22, Best Prac & Research Clinical Rheum, US.

Kremers, Therapeutic strategies in rheumatoid arthritis over a 40-year period, journal, 2004, p2366-2373, vol. 31, J of Rheumatology, US.

Lainer-Carr, Angiogenesis inhibition as a therapeutic approach for inflammatory synovitis, journal, 2007, p. 434-442, vol. 3, Nature Clinical Pract Rheumatol, US.

Matsuo, A novel melanoma-targeting peptide screened by phage display exhibits antitumor activity, journal, 2010, p1255-1264, vol. 88, J Molecular Medicine, US.

Mi, Identification of a Synovial Fibroblast-Specific Protein Transduction Domain for Delivery of Apoptotic Agents to Hyperplastic Synovium, journal, p295-305, vol. 8, Molecular Therapy, US, Aug. 2003.

Pasqualini, A Peptide Isolated from Phage Display Libraries Is a Structural and Functional Mimic of an RGD-binding Site on Integrins, journal, 1995, p1189-1196, vol. 130, J of Cellular Biology, US.

Ruoslahti, Specialization of Tumour Vasculature, journal, 2002, p83-90, vol. 2, Nature Reviews Cancer, US.

Ruoslahti, An Address Sustem in the Vasculature of Normal Tissues and Tumors, journal, 2000, p813-827, vol. 18, Annual Rev Immunology, US.

Sugahara, Coadministration of a Tumor-Penetrating Peptide Enhances the Efficacy of Cancer Drugs, journal, 2010, p1031-1035, vol. 328, Science, US.

Vasu, Modulation of Dendritic Cell Function and Cytokine Production to Prevent Thyroid Autoimmunity, journal, 2003, p389-396, vol. 36, Autoimmunity, US.

\* cited by examiner

JOINT-HOMING PEPTIDES AND USES THEREOF

CROSS-REFERENCE TO RELATED APPLICATION

This non-provisional application claims benefit of priority under 35 U.S.C. §119(a) of provisional U.S. Ser. No. 61/502,376, filed Jun. 29, 2011, now abandoned, the entirety of which is hereby incorporated by reference.

FEDERAL FUNDING LEGEND

This invention was made with government support under Grant Number AR051718 awarded by the National Institutes of Health. The government has certain rights in the invention.

BACKGROUND OF THE INVENTION

1. Field of the Invention

The present invention is in the field of arthritis and pharmacotherapy of arthritis and joint diseases. More specifically, the present invention is directed to novel peptides which home to joints and uses thereof.

2. Description of the Related Art

Rheumatoid arthritis (RA) is a T-cell-mediated autoimmune disease (1). Both the joint-resident and systemic antigens have been invoked in the pathogenesis of RA (2, 3). Furthermore, the joints are frequently targeted in pathological conditions associated with systemic autoimmunity (4). A major challenge in this regard lies in defining the mechanisms underlying the selective targeting of the joints in the face of systemic autoimmunity. The migration of pathogenic T cells and other leukocytes into the joints depends on the interaction between the leukocytes and the target organ vasculature. In addition, angiogenesis plays am important role in the disease process in RA (5, 6). Thus, targeting the blood vessels is of major interest for developing novel therapeutic interventions in this disease (5-8).

The vascular bed of individual tissues is highly specialized, with endothelial cells expressing unique molecules (9, 10). Furthermore, during the process of angiogenesis, the new blood vessels express many cell surface molecules not found in normal blood vessels. The use of in vivo screening of phage peptide display libraries has been instrumental in identifying tissue/organ-specific and disease-specific vascular markers (9, 11-13). The molecular differences in the vascular endothelium of various tissues/organs have been termed as "molecular addresses" or "zip codes" (9-11). For example, a nonapeptide was found to home to normal breast tissue and to bind to aminopeptidase P in breast vasculature (14). Similarly, peptides homing specifically to brain, kidney, lung, heart, skin, pancreas, retina, and prostate have been identified (9). In all of these tissues, the phage was localized in the blood vessels. The main target of phage-encoded peptide ligands has been the tumors (15-19); the vasculature of the inflamed joint has not been probed in that manner.

The prior art is deficient in novel peptides that home to joints as well as methods of their use. The present invention fulfills this longstanding need and desire in the art.

SUMMARY OF THE INVENTION

The present invention identified peptides that home to the inflamed joint using on the adjuvant arthritis (AA) model of human RA and performing ex vivo and in vivo enrichment and screening of the phage peptide library in arthritic Lewis rats. It was an object of the present invention to identify peptides that can distinguish between the vasculature of inflamed joints and other inflamed/uninflamed tissues, and that can inhibit the recruitment of inflammatory cells into joints. It is another object of the present invention to identify peptides with anti-angiogenic activity. Described herein is the identification of joint-homing peptides with these attributes.

In one embodiment of the present invention there is provided a peptide that homes to a joint of an animal, wherein the peptide comprises an amino acid motif selected from the group consisting of NQR and ADK.

In yet another embodiment of the present invention there is provided a method of treating a subject having an arthritic joint, comprising the step of administering to the subject a pharmacologically effective dose of the composition of the present invention.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 1A: ex vivo phage enrichment using CD31+ primary endothelial cells from arthritic rat joints (left) and titers of the phage rescued in vivo from the kidney, the lung and the joint (right). *P<0.002. FIG. 1B: Titers of specific phages, each encoding a particular peptide ADK (CRNADKFPC, SEQ ID NO: 1) (left), NQR (CLDNQRPKC, SEQ ID NO: 2) (center), or RGD (CDCRGDCFC, SEQ ID NO: 4) (right) recovered in vivo from the indicated inflamed and normal (uninflamed) tissues in the presence (open bar) or absence (filled bar) of the corresponding synthetic peptide. *P<0.002.

FIG. 2A: Binding of specific phage encoding the peptide NQR or ADK to the vascular endothelium was visualized by immunohistochemical examination of the hind paw section of the rthritic rats using the anti-T7 phage antibody. The binding of phage was tested in the presence or absence of the corresponding synthetic peptide. BV, blood vessel, L, lumen. FIG. 2B: Arthritic rats were injected with specific phage (ADK phage, left; NQR phage, center; or RGD phage, right) in the presence or absence of the corresponding synthetic peptide, and the titer of the phage recovered from the synovial tissue was assessed. *P<0.01. FIG. 2C: CD31-expressing endothelial cells were isolated from arthritic rat joints (upper) or the liver (lower) and stained with DAPI (blue), FITC-labeled peptide NQR (green), or Alexa Fluor 594-labeled anti-rat CD31 antibody (red). Also shown is the staining overlay (merge) of green and red (yellow). The inset is an enlarged view of a single cell; original magnification, 20×. FIG. 2D: LPS-stimulated HUVECs were stained with DAPI and FITC-labeled peptide NQR and observed under a fluorescence microscope, original magnification, 100×.

FIG. 3A: Group of arthritic Lewis rats (n=4 per group) were injected with a peptide (AD, NQR, or RGD) or PBS i.v. on the days indicated by the arrows either at the onset or just after the onset of arthritis. The its were monitored regularly for the disease severity, presented as "arthritic score". The difference between NQR (filled inverted triangle, 1 mg/kg) and ADK was significant (*P<0.05 from day 17 to day 21, as was the difference between NQR (filled triangle; 2 mg/kg) and ADK from day 13 to day 26 (left). The difference between NQR/RGD and PBS/ADK was significant from day 15 to day 27 (center). The difference between NQR and PBS was significant from day 15 to day 27 (right). In all three panels, the differences between other groups not specified above were not significant. Similar results were obtained in repeat experiments. FIG. 3B: Representative H&E-stained hind paw sections of a naïve rat (i), and arthritic rat treated with PBS instead of peptide (ii), an arthritic rat treated with NQR peptide (iii), and an arthritic rat treated with RGD peptide (iv) are shown. The sections were graded for histopathological features associated with arthritis. B, bone; C, cartilage, JS, joint space; SIC, synovium-infiltrating cells.

FIG. 4A: Draining lymph node leukocytes from arthritic rats were dye-tagged with PKH67 and injected i.v. into arthritic rats. One group of rats was left untreated, and the other groups were treated with ADK or NQR peptide. After 24 hours, the synovium-infiltrating cells (SICs) were harvested from the joints, subjected to cytospin, and analyzed by fluorescence microscopy (left). In parallel, another set of synovium-infiltrating cells were stained with PE-labeled anti-CD3 or anti-CD 11b/c+ antibody and analyzed by flow cytometry (right). FIG. 4B: HUVECs were cultured on Matrigel-coated wells for 24 hours in the presence of VEGF (10 ng/mL) and various concentrations (0-100 µg/mL) of NQR (left), ADK (center), and RGD (right) peptides. The branches of vessel-like tubes were counted. A reprensentative set of results is shown. *P<0.05, compared with the VEGF-alone control.

FIG. 6A: HUVECs were stimulated with VEGF and treated with the indicated concentrations of peptides. Phosphorylated ERK1/2 and Akt, as well as total ERK1/2 and Akt, were detected by Western blot analysis. FIG. 6B: Thereafter, p-ERK1/2 and p-Akt were quantified by densitometry, normalized to total ERK1/2 (left) and Akt (right), respectively, and compared with cells in serum-free medium. The results of a representative experiment from a set of three independent experiments are shown. *P<0.05, compared with the positive control.

DETAILED DESCRIPTION OF THE PRESENT INVENTION

Figure 1A:
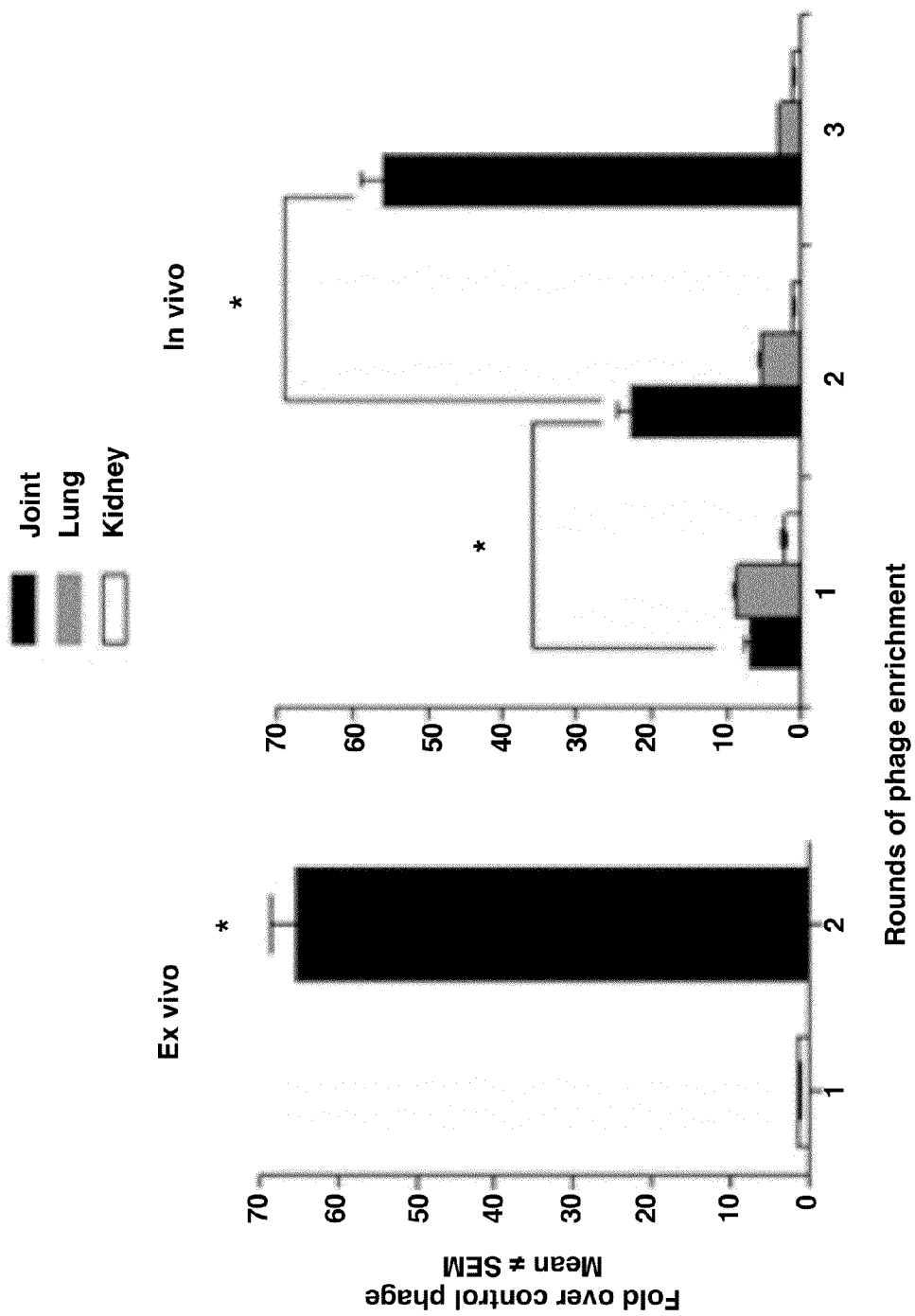
FIGS. 1A-1B show the ex vivo and in vivo enrichment of specific phage homing to the inflamed joints of Lewis rats.

The present invention is directed to a peptide that homes to a joint of an animal, wherein said peptide comprises an amino acid motif selected from the group consisting of NQR and ADK. Representative examples of peptides that home to a joint of an animal and comprise an amino acid motif of NQR and ADK include but are not limited to the sequence CRNADKFPC (SEQ ID No. 1), a peptide having a sequence at least 77% identical to CRNADKFPC (SEQ ID No. 1) a peptide having a sequence at least 88% identical to CRNADKFPC (SEQ ID No. 1), a peptide having the sequence CLDNQRPKC (SEQ ID No. 2), a peptide having a sequence at least 77% identical to CLDNQRPKC (SEQ ID No. 2) and a peptide having a sequence at least 88% identical to CLDNQRPKC (SEQ ID No. 2).

The present invention is further directed to a composition, comprising the peptide described herein. The peptide comprising an amino acid motif of NQR and ADK directs the composition to selectively home to regenerating tissue, a site of injury, a site of inflammation or a site of arthritis. In one aspect, the composition may further comprise a co-composition, wherein the peptide and the co-composition are not covalently coupled or non-covalently associated with each other. In a separate embodiment of this composition, the peptide and the co-composition are chemically conjugated or bound to each other.

Generally, the compositions of the present invention contain the peptide comprising an amino acid motif of NQR and ADK and a co-composition so that the overall composition may be used to beneficially treat a variety of inflammatory or autoimmune pathophysiological states. Thus, for example, the composition may be directed to selectively home to regenerating tissue, a site of injury, a site of inflammation or a site of arthritis.

Representative examples of co-compositions include but are not limited to a therapeutic agent, a therapeutic protein, a therapeutic compound, a therapeutic composition, a chemotherapeutic agent, a cancer chemotherapeutic agent, a toxin, a cytotoxic agent, imatinib, an anti-angiogenic agent, an anti-inflammatory agent, an anti-arthritic agent, a TGF-.beta. inhibitor, decorin, a systemic vasodilator, an anti-coagulant, tissue factor pathway inhibitor (TFPI), site-inactivated factor Vila, a .beta.-2 agonist, salmeterol, formoterol, N-Acetylcysteine (NAC), Superoxide Dismutase (SOD), a superoxide dismutase mimetic, EUK-8, an endothelin (ET-1) receptor antagonist, a prostacyclin derivative, a phosphodiesterase type 5 inhibitor, Ketoconazole, a small interfering RNA (siRNA), a microRNA (miRNA), a polypeptide, a nucleic acid molecule, a small molecule, a carrier, a vehicle, a virus, a phage, a viral particle, a phage particle, a viral capsid, a phage capsid, a virus-like particle, a liposome, bone remodeling agents, tissue regenerating agents, a micelle, a bead, a nanoparticle, a microparticle, a detectable agent, a contrast agent, an imaging agent, a label, a labeling agent, a fluorophore, fluorescein, rhodamine, FAM, a radionuclide, indium-111, technetium-99, carbon-11, carbon-13, a disease-modifying antirheumatic drug, an analgesic or a combination.

Representative examples of anti-angiogenic agents include but are not limited to thrombospondin, angiostatin5, pigment epithelium-drived factor, angiotensin, laminin peptides, fibronectin peptides, plasminogen activator inhibitors, tissue metalloproteinase inhibitors, interferons, interleukin 12, platelet factor 4, IP-10, Gro-.beta., thrombospondin, 2-methoxyoestradiol, proliferin-related protein, carboxiamidotriazole, CM101, Marimastat, pentosan polysulphate, angiopoietin 2 (Regeneron), interferon-alpha, herbimycin A, PNU145156E, 16K Prolactin fragment, Linomide, thalidomide, pentoxifylline, genistein, TNP-470, endostatin, paclitaxel, Docetaxel, polyamines, a proteasome inhibitor, a kinase inhibitor, a signaling peptide, accutin, cidofovir, vincristine, bleomycin, AGM-1470, platelet factor 4 and minocycline.

Representative examples of anti-inflammatory agents include but are not limited to steroids, such as cortisone, glucocorticoids, prednisone, prednisolone, Hydrocortisone (Cortisol), Cortisone acetate, Methylprednisolone, Dexamethasone, Betamethasone, Triamcinolone, Beclometasone, and Fludrocortisone acetate; non-steroidal anti-inflammatory drug (NSAIDs), ibuprofen, naproxen, meloxicam, etodolac, nabumetone, sulindac, tolementin, choline magnesium salicylate, diclofenac, diflusinal, indomethicin, Ketoprofen, Oxaprozin, piroxicam, and nimesulide, Salicylates, Aspirin (acetylsalicylic acid), Diflunisal, Salsalate, p-amino phenol derivatives, Paracetamol, phenacetin, Propionic acid derivatives, Ibuprofen, Naproxen, Fenoprofen, Ketoprofen, Flurbiprofen, Oxaprozin, Loxoprofen, Acetic acid derivatives, Indomethacin, Sulindac, Etodolac, Ketorolac, Diclofenac, Nabumetone, Enolic acid (Oxicam) derivatives, Piroxicam, Meloxicam, Tenoxicam, Droxicam, Lornoxicam, Isoxicam, Fenamic acid derivatives (Fenamates), Mefenamic acid, Meclofenamic acid, Flufenamic acid, Tolfenamic acid, Selective COX-2 inhibitors (Coxibs), Celecoxib, Rofecoxib, Valdecoxib, Parecoxib, Lumiracoxib, Etoricoxib, Firocoxib, Sulphonanilides, Nimesulide, and Licofelone.

Representative examples of analgesic agents include but are not limited to NSAIDs, COX-2 inhibitors, Celecoxib, Rofecoxib, Valdecoxib, Parecoxib, Lumiracoxib, Etoricoxib, Firocoxib, acetaminophen, opiates, Dextropropoxyphene, Codeine, Tramadol, Anileridine, Pethidine, Hydrocodone, Morphine, Oxycodone, Methadone, Diacetylmorphine, Hydromorphone, Oxymorphone, Levorphanol, Buprenorphine, Fentanyl, Sufentanyl, Etorphine, Carfentanil, dihydromorphine, dihydrocodeine, Thebaine, Papaverine, diproqualone, Flupirtine, Tricyclic antidepressants, and lidocaine.

Representative examples of disease-modifying antirheumatic drugs include but are not limited to mycophenolate mofetil (CellCept), calcineurin inhibitors, cyclosporine, sirolimus, everolimus, oral retinoids, azathioprine, fumeric acid esters, D-penicillamine, cyclophosphamide, immunoadsorption column, Prosorba(r) column, a gold salt, auranofin, sodium aurothiomalate (Myocrisin), hydroxychloroquine, chloroquine, leflunomide, methotrexate (MTX), minocycline, sulfasalazine (SSZ), tumor necrosis factor alpha (TNFa) blockers, etanercept (Enbrel), infliximab (Remicade), adalimumab (Humira), certolizumab pegol (Cimzia), golimumab (Simponi)), Interleukin 1 (IL-1) blockers, e.g., anakinra (Kineret), monoclonal antibodies against B cells, rituximab (Rituxan)), T cell costimulation blockers, abatacept (Orencia), Interleukin 6 (IL-6) blockers, tocilizumab, RoActemra, and Actemra.

A person having ordinary skill in this art would readily recognize that the compositions of the present invention may take a variety of forms, such as, as described above, a liposome, a vesicle or a nanoparticle. A person having ordinary skill in this art would further readily recognize that that chemical forms such as liposomes or nanoparticles, including there construction and administration, have been well known in the art. For example, a person having ordinary skill in this art would readily recognize that a liposome or nanoparticle may be coated on or within its surface with the peptides described herein so as to selectively target sites of interest for specific therapeutic or diagnostic purposes.

The present invention is further directed to a method of treating a subject having an arthritic joint, comprising the step of administering to said subject a pharmacologically effective dose of the composition comprising a peptide with a sequence selected from the group consisting of CLDNQRPKC (SEQ ID No. 2), a peptide having a sequence at least 77% identical to CLDNQRPKC (SEQ ID No. 2) and a peptide having a sequence at least 88% identical to CLDNQRPKC (SEQ ID No. 2).

The present invention is further directed to a method of treating a subject having an arthritic joint, comprising the step of administering to said subject a pharmacologically effective dose of the composition further comprising a co-composition, wherein the peptide and the co-composition are not covalently coupled or non-covalently associated with each other. Representative examples of said peptides and said co-compositions are described in detail supra.

The present invention is further directed to a method of treating a subject having an arthritic joint, comprising the step of administering to said subject a pharmacologically effective dose of the composition wherein said liposome or said nanoparticle is coated on its surface with the peptide with a sequence selected from the group consisting of CLDNQRPKC (SEQ ID NO. 2), a peptide having a sequence at least 77% identical to CLDNQRPKC (SEQ ID NO. 2) and a peptide having a sequence at least 88% identical to CLDNQRPKC (SEQ ID NO. 2).

DEFINITIONS

Unless otherwise noted, technical terms are used according to conventional usage. Definitions of common scientific technical terms may be found, for example, in Mcgraw-hill Dictionary of Scientific & Technical Terms published by Mcgraw-hill Healthcare Management Group; Benjamin Lewin, Genes VIII, published by Oxford University Press; Kendrew et al. (eds.), The Encyclopedia of Molecular Biology, published by Blackwell Publishers; and Robert A. Meyers (ed.), Molecular Biology and Biotechnology: a Comprehensive Desk Reference, published by Wiley, John & Sons, Inc; and other similar technical references.

As used herein the specification, "a" or "an" may mean one or more. As used herein in the claim(s), when used in conjunction with the word "comprising", the words "a" or "an" may mean one or more than one. As used herein "another" may mean at least a second or more. Furthermore, unless otherwise required by context, singular terms shall include pluralities and plural terms shall include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "pharmacologically effective dose" (or a derivative or variation thereof) is an amount of a peptide of the invention or composition containing the same that alleviates, totally or partially, the pathophysiological effects of a treatment indication of the invention (including, for example, treatment of an inflammatory, autoimmune or arthritic condition or a subject at risk of developing a an inflammatory, autoimmune or arthritic condition). Unless otherwise indicated when referring to the administration of a peptide of the invention or composition containing the same, said peptide of the invention or composition containing the same is administered at a concentration that is a pharmacologically effective dose. A pharmacologically effective dose will depend upon, for example, subject size, gender, magnitude of the associated disease, condition, or injury, and genetic or non-genetic factors associated individual pharmacokinetic or pharmacodynamic properties of the administered antibacterial peptide of the invention or composition containing the same. For a given subject in need thereof, a pharmacologically effective dose can be determined by one of ordinary skill in the art and by methods known to one of ordinary skill in the art.

As used herein, the term "subject" refers to any recipient of the peptides or therapeutic compositions comprising the same, as described herein.

In other embodiments, the compounds of the invention comprise one or more conservative amino acid substitutions. Conservative substitutions, in which an amino acid is exchanged for another having similar properties, can be made in a compound of the invention by techniques well known by one of ordinary skill in the art. Conservative amino acid substitutions typically fall in the range of about 1 to 2 amino acid residues. Guidance in determining which amino acid residues can be substituted without activity or immunological properties can be found using computer programs well known in the art, such as DNASTAR software, or in Dayhoff et al. (1978) in Atlas of Protein Sequence and Structure (Natl. Biomed. Res. Found., Washington, D.C.). Amino acid substitutions conservative in nature are when, for example, the substituted amino acid has similar structural and/or chemical properties (including, for example, molecular weight, polarity, isoelectric point, hydrophilicity, hydrophobicity, charge, etc.) (see, for example, U.S. Pat. No. 7,098,015, which along with all other references cited herein is incorporated by reference in its entirety). Examples of conservative replacements are substitution of a leucine with an isoleucine or valine, an aspartate with a glutamate, or a threonine with a serine. Specifically, amino acids are generally divided into families: (1) acidic—aspartate and glutamate; (2) basic—lysine, arginine, histidine; (3) non-polar—alanine, valine, leucine, isoleucine, proline, phenylalanine, methionine, tryptophan; (4) uncharged polar—glycine, asparagine, glutamine, cysteine, serine threonine, and tyrosine; (5) aromatic amino acids—phenylalanine, tryptophan, and tyrosine.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Animals

Lewis (LEW/SsNHsd; RT.1$^l$) rats were purchased from Harlan. Four-to-six week old male rats were used. The rats were housed in the vivarium of the University of Maryland School of Medicine and were handled in accordance with the school's Institutional Animal Care and Use Committee.

Example 2

Phage Library and Ex Vivo/In Vivo Phage Screening

The CX7C library displayed on the T7Selected415-1 phage (Novagen) was prepared as described previously (9, 14). This library was subjected to sequential ex vivo and in vivo phage selection. For the ex vivo selection, $1 \times 10^7$ cells from the harvested synovial tissue were incubated overnight at at 4° C. with $5 \times 10^{10}$ plaque-forming units (pfu) of a CX7C library. These cells were washed to remove unbound phage and then incubated with mouse anti-rat CD31 antibody. The CD31+ cells were then isolated using rat anti-mous IgG1 microbeads. Phage bound to the CD31+ cells was rescued, tittered, and amplified using *Escherichia coli* BL21

For the in vivo selection, the phage pool ($5 \times 10^{10}$ pfu) from the foregoing screen was injected into an arthritic Lewis rat via the tail vein under anesthesia. The phage was allowed to circulate for 10 min, after which the rat was perfused through the left ventricle with PBS containing 1% BSA to clear unbound phage in the vascular lumen. The synovial tissue along with the control tissues, e.g., kidney, lung or skin, was excised, and the phage thus recovered from the synovium was reinjected into another arthritic Lewis rat at a comparable disease stage. This procedure was repeated three times. In each experiment, the nonrecombinant phage was injected as a control into a separate rat for determining the relative selectivity of the phage for a given tissue. After the last round of in vivo selection, the phage clones were chosen at random and grown as individual phage in liquid culture. Thereafter, the recombinant phage's coding region isert was amplified by PCR (PTC-200 Peltier Thermal Cycler; MJ Research) and subjected to automatic DNA sequencing at the University of Maryland School of Medicine's Biopolymer/Genomic Core Facility.

Example 3

Synthetic Peptides

Peptides were synthesized at the University of Maryland School of Medicine's Biopolymer/Genomic Core Facility, GenScript Corporation, and Peptide International. For easy description, each peptide was given an abbreviated name, e.g., ADK or NQR.

The complete amino acid sequences of the peptides are as follows: ADK peptide, CRNADKFPC (SEQ ID NO: 1); NQR peptide, CLDNQRPKC (SEQ ID NO: 2); RGD peptide, RGDfK (SEQ ID NO: 3). The RGDfK peptide was chosen over CDCRGDCFC (SEQ ID NO: 4), i.e., RCD-4C (SEQ ID NO: 4) because of the relative ease of synthesis, and the two peptides have a similar affinity for αv integrins (21). In addition, the RGDfK (SEQ ID NO: 3) peptide may be more resistant to proteolysis because of its small ring and D-amino acid residue.

Example 4

Determination of Antiarthritic Activity of Phage-Derived Peptides

The synthetic peptide corresponding to the selected phage-encoded peptide was diluted in PBS and injected i.v. into Lewis rats beginning either at the onset or just after the onset of arthritis after Mtb injection. The peptide was injected to rats on alternate days at a dose of 1 or 2 mg/kg body weight. A total of three or four injections were given to each rat. Control animals received an equal volume of PBS. All rats were graded regularly for clinical signs of arthritis (36). The hind paws of these rats were harvested and processed for histopathological examination.

Example 5

Isolation, Labeling, and In Vivo Migration of Leukocytes

The draining lymph nodes of rats were harvested on day 14 after immunization with Mtb and then minced to prepare single-cell suspensions. These cells were then washed twice with HBSS (Sigma-Aldrich) and dye-tagged with PKH67 (Sigma-Aldrich). In brief, viable cells ($2 \times 10^7$) were suspended in medium without serum and mixed with PKH67 ($4 \times 10^6$ molar). After incubation at 25° C. for 2-5 min with occasional shaking, the staining reaction was stopped with serum. Then the cells were washed thoroughly before being suspended in medium for injection into rats. Labeling of the cells was monitored using fluorescence microscope after cytospinning. Labeled cells ($1 \times 10^7$) were injected i.v. into the tail vein of arthritic Lewis rats. The rats were killed 24 h later, and single-cell suspensions of synovial cells was prepared as described above. These cells were then stained with labeled antibodies against CD3 (PharMingen) or CD11b/c (PharMingen), followed by analysis by flow cytometry (BD Biosciences LSR II).

Example 6

Assay Measuring the Attachment of HUVECs to Vitronectin

The attachment of HUVECs to vitrnectin was quantified as described (37, 38). Microtiter wells were coated overnight at 4° C. with 2 µg/mL of vitronectin (BD Biosciences). These wells were then blocked for 1 h at 37° C. with 10 mg/mL of BSA (Sigma-Aldrich). In parallel, HUVECs ($1.5 \times 10^5$ cells/mL) suspended in F-12K medium containing 10% FBS were incubated for 15 min at 37° C. with different concentrations (30-800 µg/mL) of NQR, ADK, or RGD peptide. Thereafter, this cell suspension 100 µL/well) was added to the vitronectin-coated wells, followed by incubation at 37° C. for 1 h. After washing, the number of attached cells was determined using crystal violet (Fisher Scientific).

Example 7

Isolation of Endothelial Cells from the Synovial Tissue of the Joints of Arthritic Rats The synovial tissue harvested from the ankle joints of arthritic rats was digested for 1 h at 37° C. in HBSS containing 3 mg/mL of collagenase 1A (Sigma-Aldrich), 1 mg/mL of hyaluronidase IV-S (Sigma-Aldrich), 0.1 mg/mL of DNase II (Sigma-Aldrich), 1% FBS, and 5% Hepes. The digested tissue was filtered through a nylon mesh and washed extensively with PBS. Magnetic bead separation was used to isolate the CD31+ endothelial cells. In brief, the suspended cells were incubated on ice with mouse anti-rat CD31 antibody (BD PharMingen) for 5 min, followed by the addition of rat anti-mouse IgG1 microbeads (Miltenyi Biotec). After 15 min, the cell suspension was loaded onto a MACS column placed in the magnetic field of a MACS separator (Miltenyi Biotec). The unlabeled cells were washed away, and the labeled cells were eluted and collected as the selected cell fraction.

Example 8

Immunohistochemical Examination of Cells/Tissues

Endothelial cells from the synovial tissue and other control tissues were seeded on coverslips in M199 medium plus 1% BSA for 2 h, followed by the addition of fluorescein-conjugated peptide (5 µmol/L) onto the cells. After incubation on ice for 30 min, the cells were washed three times with PBS and then incubated with anti-rat CD31 antibody (1:100) overnight at 4° C., followed by incubation with the secondary antibody, Alexa Fluor-conjugated goat antimouse IgG (1:1, 000). The slides were washed three times with PBS, mounted with Prolong Gold anti-fade reagent, and examined under microscope. For detection of phage in tissues, rats were injected with $10^9$ pfu of phage and perfused under anesthesia as described above. The hind paws of rats were removed and tissue sections were prepared as described below. An antibody against T7 phage was used for staining, followed by staining with peroxidase-conjugated secondary antibody.

Example 9

Induction and Evaluation of AA

AA was induced in Lewis rats by immunizing them with 1 mg/rat of heat-killed *M. tuberculosis* H37Ra (Mtb; Difco) in 200 µL of mineral oil (Sigma-Aldrich) via s.c. injection at the base of the tail. Beginning on day 7 after immunization, the rats were observed regularly for signs of arthritis in the paws. The severity of arthritis was evaluated based on erythema and swelling as described previously. The highest score for each paw was 4, and the total maximum score for each rat was 16. The course of AA in the Lewis rat involved the following phases: incubation (days 0-8), onset (days 9-11), peak (days 15-18), and recovery (days 21-27).

Example 10

Histopathological Evaluation of Hind Paw Joints of Rats

Hind paws of rats were harvested, skinned, and fixed with 10% phosphate buffered formalin (Fisher Scientific) for 3-7 d (1). Then the paws were decalcified in formic acid (Fisher Scientific), embedded in paraffin, and sectioned longitudinally (820 microtome; Fisher Scientific). Tissue sections (5 µm) were placed on a glass slide, stained with H&E (Sigma-Aldrich), and assessed for morphological changes and cellular infiltrates.

Example 11

Testing the Effects of Peptides on Tubule Formation

HUVECs ($1 \times 10^4$) were cultured in 80 µL/well of growth factor-reduced Matrigel (BD Biosciences) in a 96-well plate in 100 µL/well of F-12K medium (with no supplements). These cells were then treated for 20 h with VEGF (R&D Systems) in the presence or absence of different concentrations of peptides (NQR, ADK, or RGD). Tubule formation was observed under a microscope, quantitated, and photographed.

Example 12

Determining the Effects of Peptides on Cell Signaling

HUVECs were grown in F-12K medium in the presence of endothelial cell growth supplement (ECGS) (BD Biosciences) and 15% FBS. Confluent cells were starved in basal medium (without ECGS and FBS) for 6 h. Then the cells were pretreated for 1 h with different concentrations (10, 50, and 100 µg/mL) of a peptide (NQR, ADK, or RGD) in fresh basal medium, followed by treatment with VEGF (10 ng/mL) for another 20 min. The conditional medium was discarded, and the cells were lysed using a lysis buffer containing protease inhibitors and phosphatase inhibitors. The cell lysate was then centrifuged, and the resulting supernatant was used for analysis of signaling molecules using specific antibodies to human pERK1/2, ERK1/2, pAkt, Akt, and GAPDH (Cell Signaling Technology) by Western blot analysis. The intensity of the bands in the gel was quantified by densitometry. The levels of p-ERK1/2 and p-Akt were normalized to total ERK1/2 and Akt, respectively, and compared with cells in serum-free medium.

Example 13

Statistical Analysis

Data are expressed as mean±SEM of multiple experiments. ANOVA and the unpaired Student t test were used for statistical analysis. A P value<0.05 was considered significant.

Example 14

Results

The vasculature of arthritic joints of Lewis rats was probed using a phage peptide display library. Phages specific for arthritic joints were identified and isolated using a combination of ex vivo and in vivo phage screening. For ex vivo screening, CD31-expressing endothelial cells from the joints of an arthritic rat were used. Two rounds of ex vivo enrichment produced a phage pool that bound 66-fold more efficiently to the endothelial cells compared with the nonrecombinant phage (FIG. 1A, Left).

The ex vivo selected phage was injected i.v. into an arthritic rat, and subsequent three rounds of in vivo selection yielded a 53-fold enrichment of the phage recovered from the synovial tissue, whereas no enrichment was observed in the control tissues, namely the lung and the kidney (FIG. 1A, Right). Three phage insert sequences ADK (CRNADKFPC, SEQ ID NO: 1), NQR (CLDNQRPK, SEQ ID NO: 2) and RGD-4C (CDCRGDCFC; SEQ ID NO: 4) were enriched in two independent experiments, which yielded 20-50 phage clones with these sequences. The RGD-4C peptide has been identified in previous phage screens that used purified integrins or tumors as the target (15, 20). As described above, an alternative RGD peptide RGDfK (SEQ ID NO: 3) was used, which has an affinity for αv integrins similar to that of RGD-4C (21), as a positive control in most of the experiments.

Figure 1B:
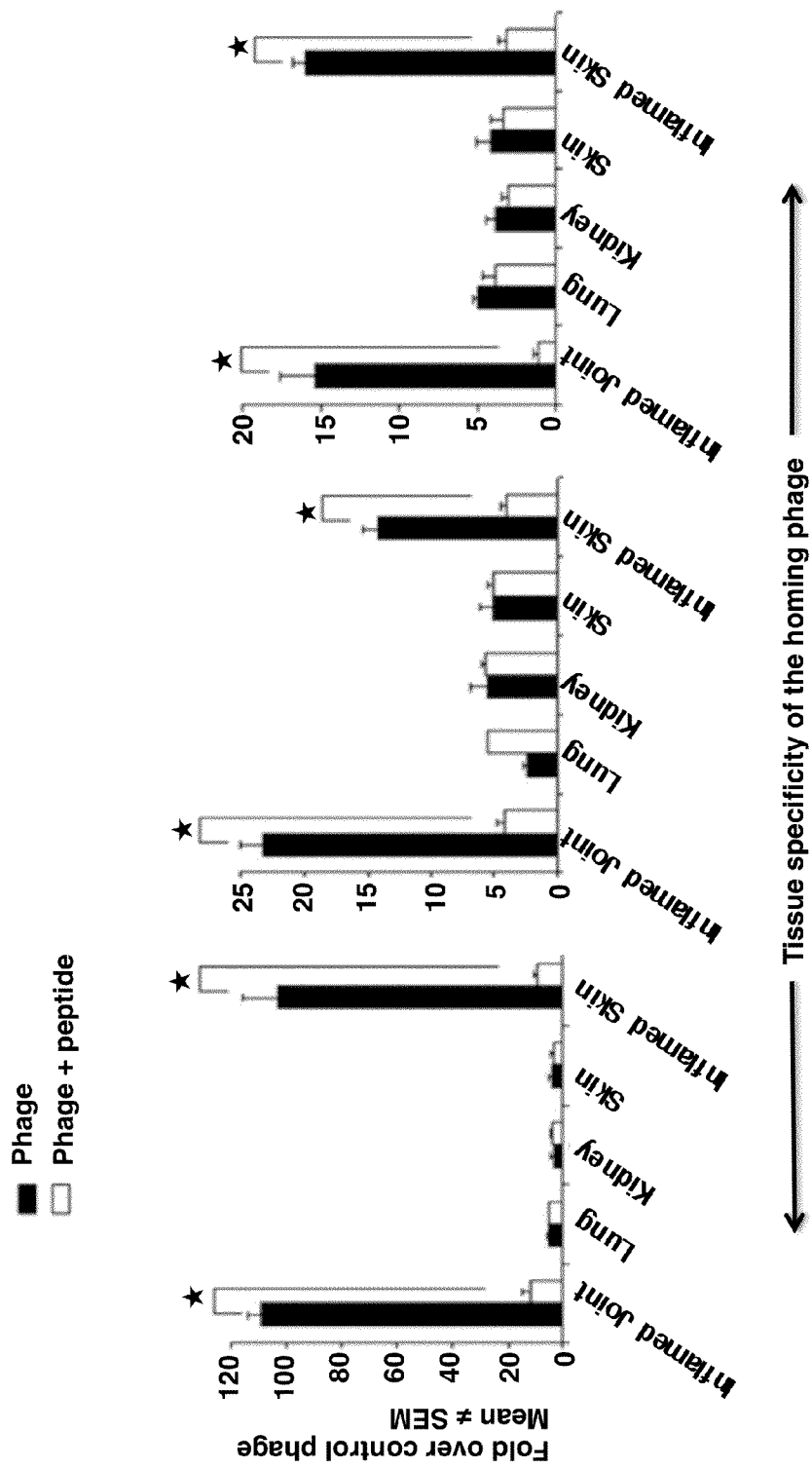

Compared with the nonrecombinant control phage, the selected phage encoding the three peptides (one each) accumulated in the inflamed joints by 109-fold more for ADK, 23-fold more for NQR, and 15-fold more for RGD (FIG. 1B). The accumulation within inflamed skin was 103-fold greater, 14-fold greater, and 16-fold greater, respectively. Thus, of the three phages, the NQR-encoding phage showed partial preference for inflamed joints relative to inflamed skin. None of these three phage clones showed significant binding to various normal (noninflamed) tissues tested, including the skin (FIG. 1B). Thus, the three phage clones selected demonstrated specificity for inflamed joints and skin, suggesting the presence of target molecules that are preferentially expressed during inflammation.

Figure 2A:
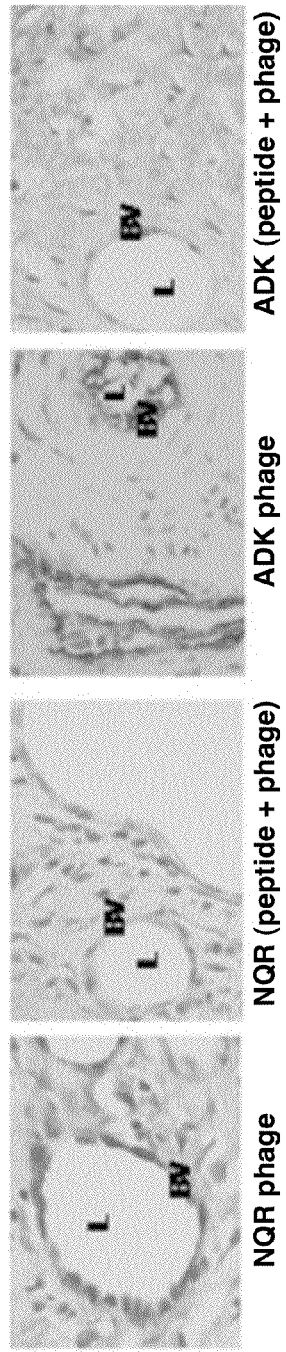
FIGS. 2A-2D show that selected phages bind to synovial vasculature of the inflamed joint, and the phage-encoded peptides inhibit phage binding and colocalize with CD31 on endothelial cells.
Figure 2B:
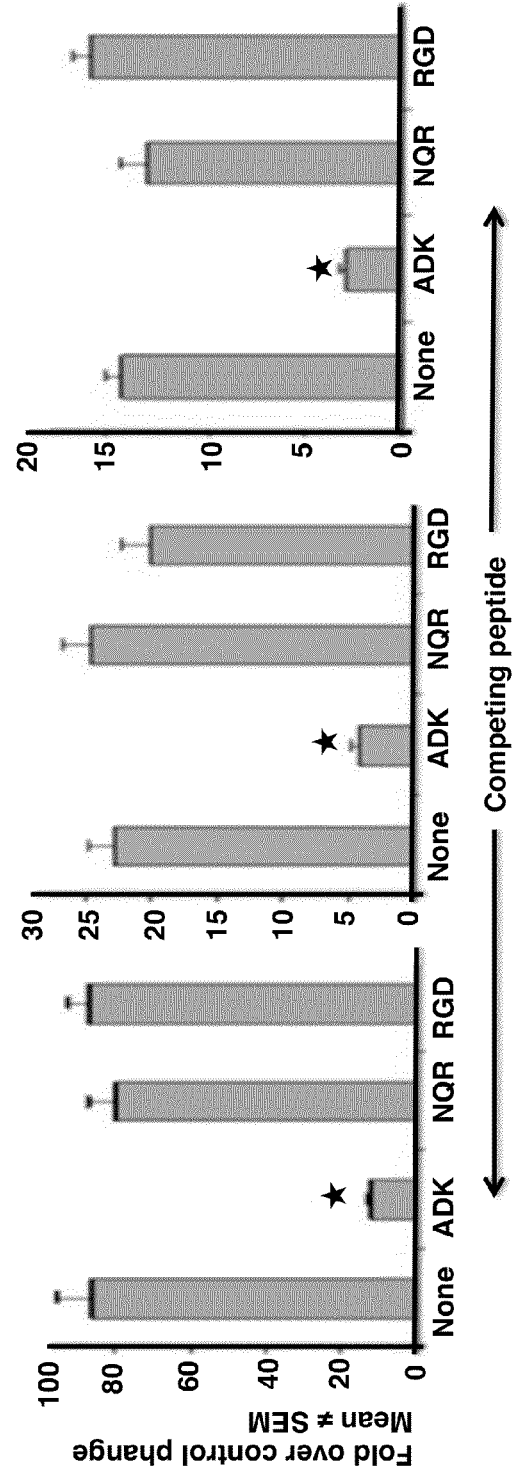

The specificity of binding of the phage clones to the vascular endothelium of inflamed joints was further established. Examination of the hind paw sections of the phage-injected arthritic rats showed preferential binding of the selected phage clones to the joint vasculature (FIG. 2A). This phage binding was inhibited by the cognate synthetic peptide but not the unrelated peptides when administered to rats before injection of the phage (FIG. 2B). Furthermore, no binding of the phage clones to the uninflamed normal joints of Lewis rats was detected. These results demonstrate the specificity of binding of the phages/peptides for the vasculature of the inflamed joint and suggest that they each bind to different receptors.

Figure 2C:
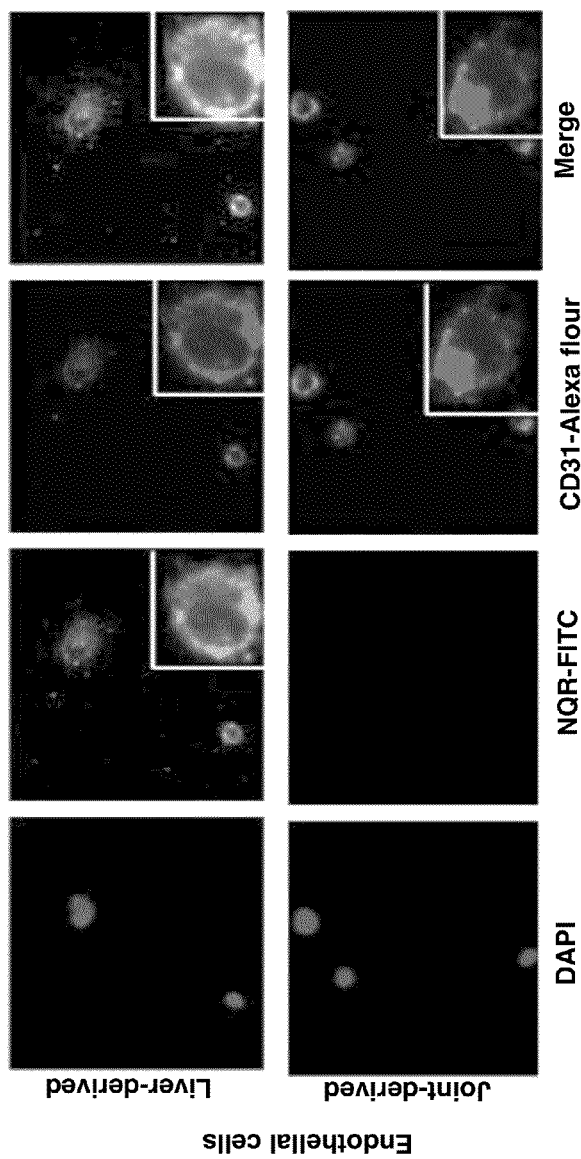
Figure 2D:
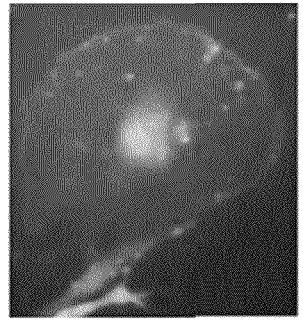

The specificity was further validated by testing the binding of fluorescein-labeled NQR peptide to CD31-expressing endothelial cells from an arthritic rat joint and from a control tissue, the liver. The NQR peptide bound specifically to the joint-derived, but not to the liver-derived, endothelial cells (FIG. 2C). Furthermore, the NQR peptide colocalized with CD31 on the joint-derived endothelial cells. Similar results were found when using the ADK peptide. In addition, NQR peptide was transported across the cell membrane into the cytoplasm and the nucleus, with most peptide accumulating in the perinuclear area by 45 min after addition to the cells (FIG. 2D). The internalized NQR might be involved in regulation of gene expression and interaction with the signaling pathway.

Figure 3A:
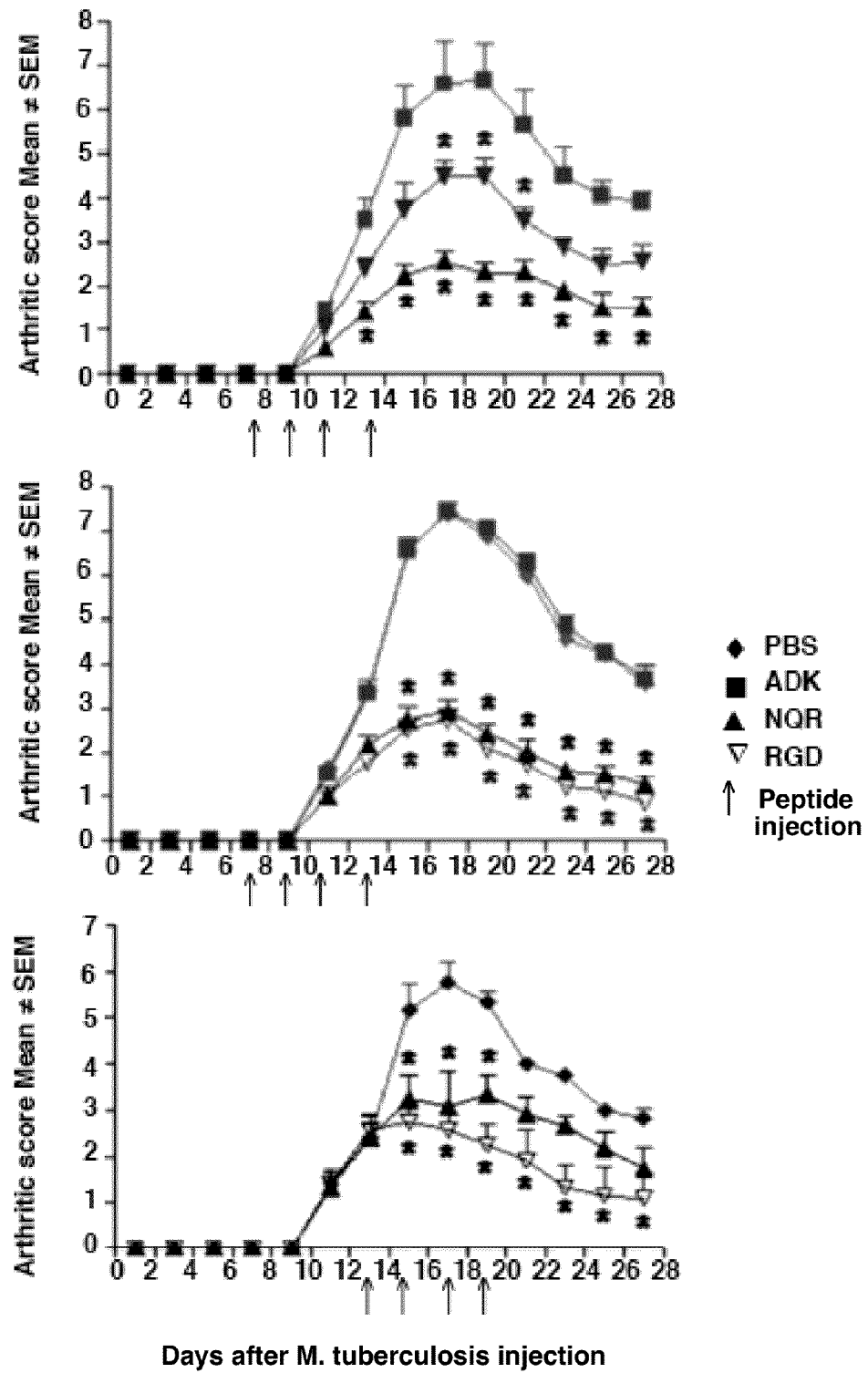
FIGS. 3A-3B show that treatment of arthritic Lewis rats with the phage-encoded peptides suppresses adjuvant arthritis.
Figure 3B:
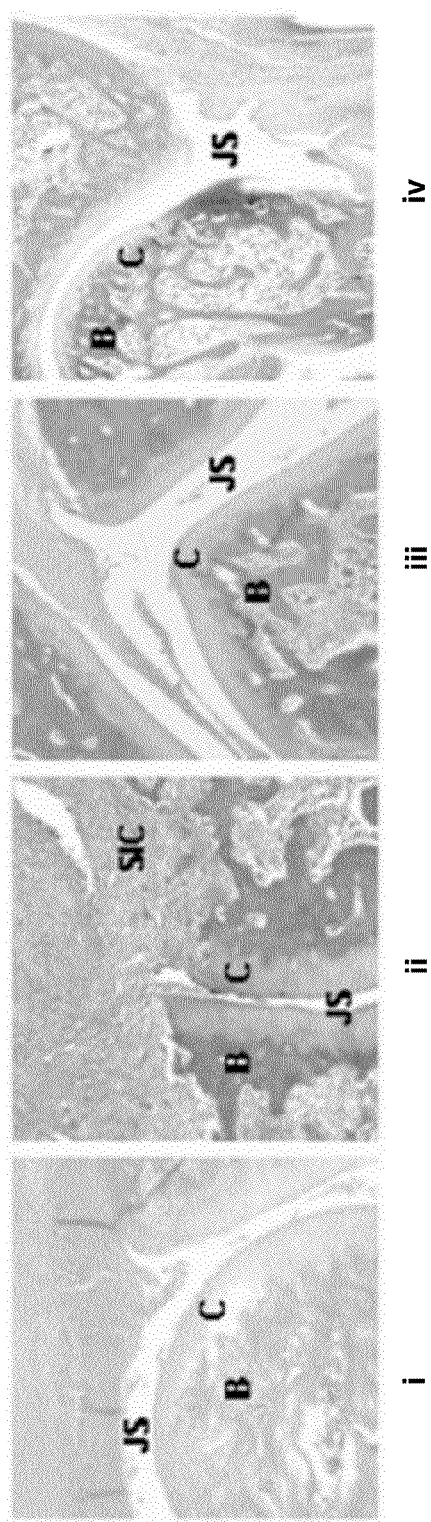
Figure 4A:
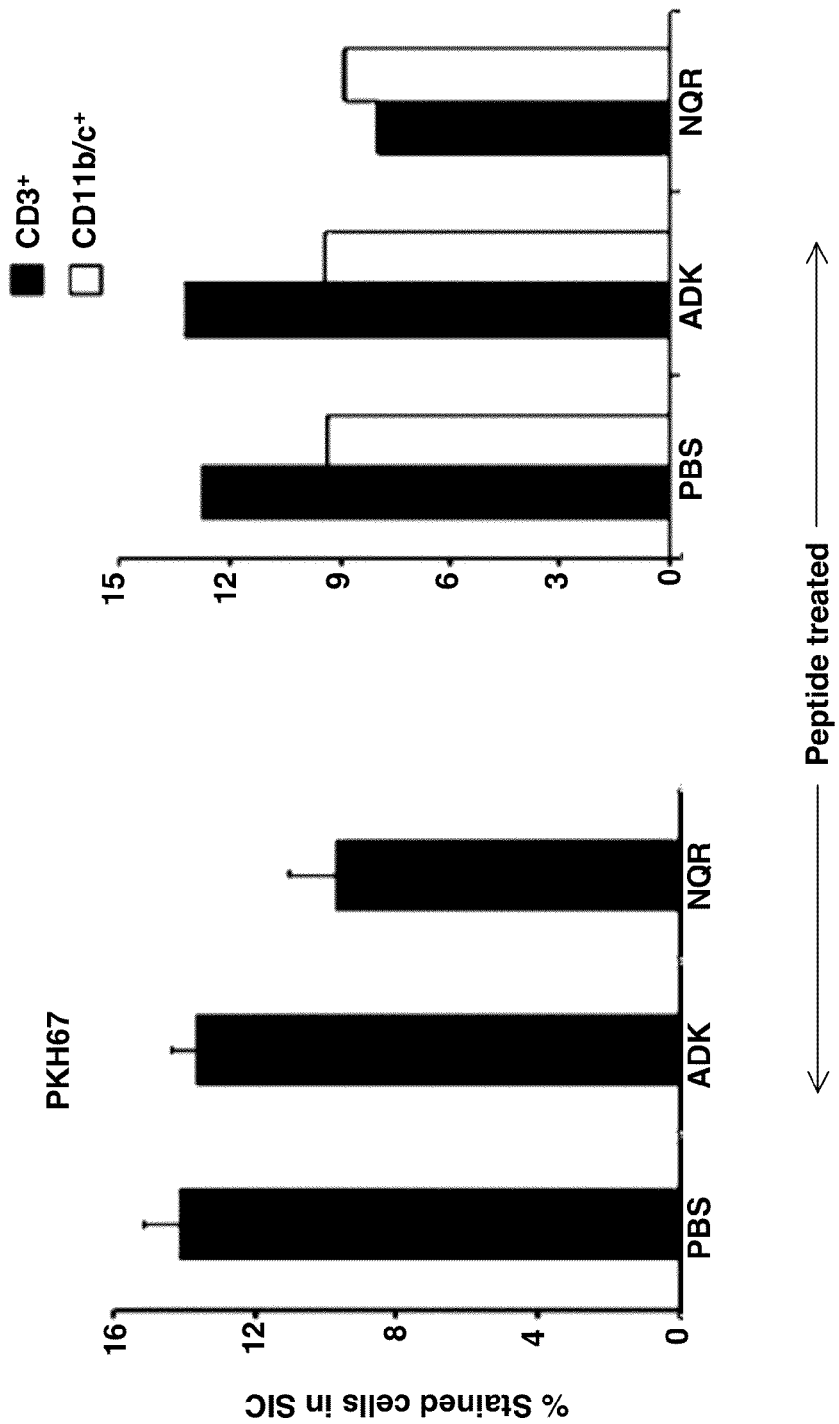
FIGS. 4A-4B show that phage-encoded peptides inhibit the migration of CD3+ T cells into the joints and endothelial tube formation.

The inflamed joint-homing peptides was also examined for their antiarthritic activity using the AA model. Intravenous injection of the peptides into rats around the time of onset of arthritis showed that the NQR peptide, but not the ADK peptide, suppressed the arthritic process in a dose-dependent manner (FIG. 3A, Left). The RGD peptide also suppressed arthritis; NQR and RGD were equally effective in this regard (FIG. 3A, Middle). These two peptides also were effective in down-modulating arthritis when injected just after the onset of AA (FIG. 3A, Right). The joints of the NQR-treated arthritic rats showed much less damage than the joints of arthritic rats treated with PBS instead of a peptide (FIG. 3B). Similar results were obtained in RGD-treated rats. Importantly, NQR-treated animals showed significantly less leukocyte infiltration into the joints than nontreated arthritic or ADK-treated arthritic rats (FIG. 4A). This effect was more marked on CD3+ T cells than on CD11b/c+ myeloid cells.

Figure 4B:
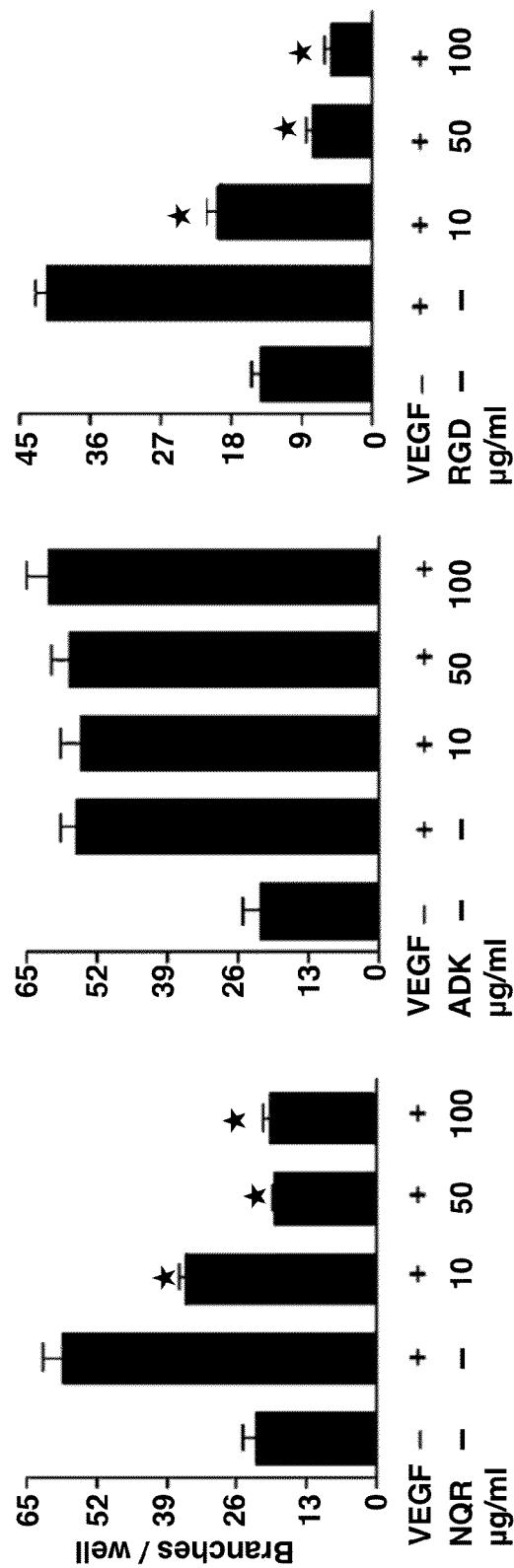

To gain further insight into the antiarthritic activity of the NQR peptide, the effects of NQR, ADK, and RGD peptides on endothelial cell tube formation were examined, which reflects the process of angiogenesis. The NQR and RGD peptides inhibited tube formation, whereas ADK peptide had no effect (FIG. 4B). This pattern was directly correlated with the antiarthritic activity of the NQR and RGD peptides and the lack of such activity by the ADK peptide (FIGS. 3A-3B).

Figure 5:
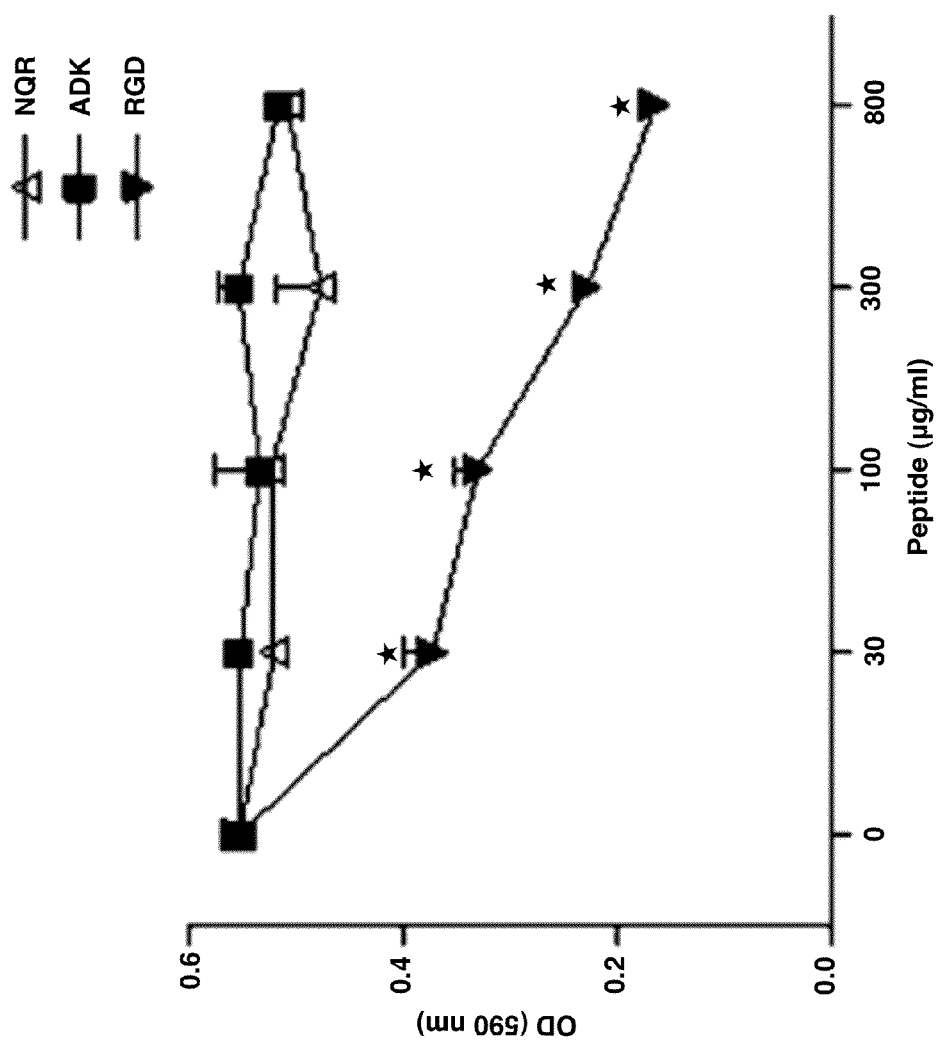
FIG. 5 shows the effect of joint-homing peptides on cell attachment to vitronectin. HUVECs were first suspended in F-12K medium containing the indicated concentrations of NQR, AK or RGD peptide and then incubated for 1 h in microtiter wells coated with vitronectin. The number of cells that attached to vitronectin was quantified. The results of three independent experiments are shown. *P<0.05, compared with the baseline control.

As shown in FIG. 2, both the NQR and ADK peptides bound to endothelial cells. The endothelial cell surface receptors involved in binding are not yet defined. Because peptides containing the RGD motif are known to bind to αv integrins and inhibit the attachment of cells to RGD-containing adhesive proteins, such as vitronectin, the NQR and ADK peptides were tested in a cell attachment assay. Neither peptide had any effect on the attachment of human umbilical vein endothelial cells (HUVECs) to vitronectin (FIG. 5). In contrast, the RGD peptide significantly inhibited cell attachment, and the effect was dose-dependent. These results suggest that the antiarthritic activity of the NQR peptide is not mediated by αv integrin binding.

Figure 6A:
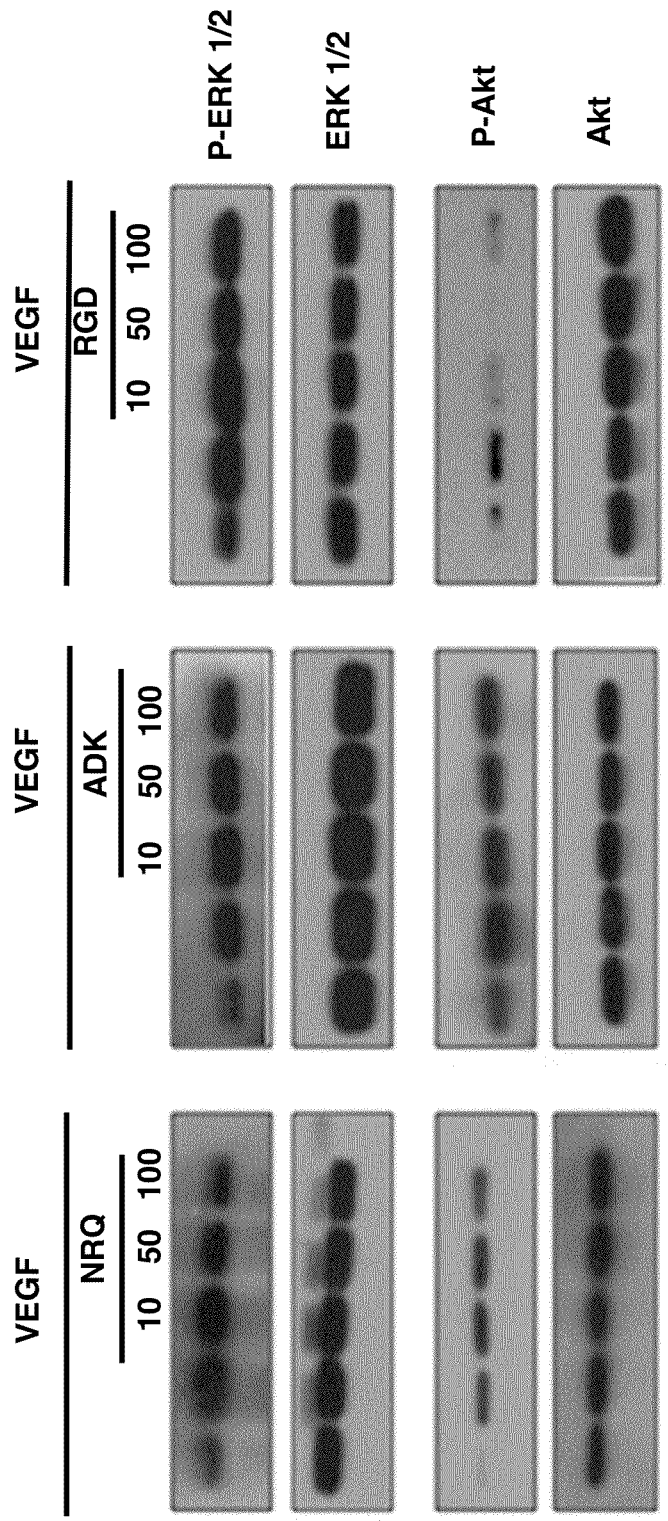
FIGS. 6A-6B show that joint-homing peptides differentially modulate the VEGF-induced signaling events.
Figure 6B:
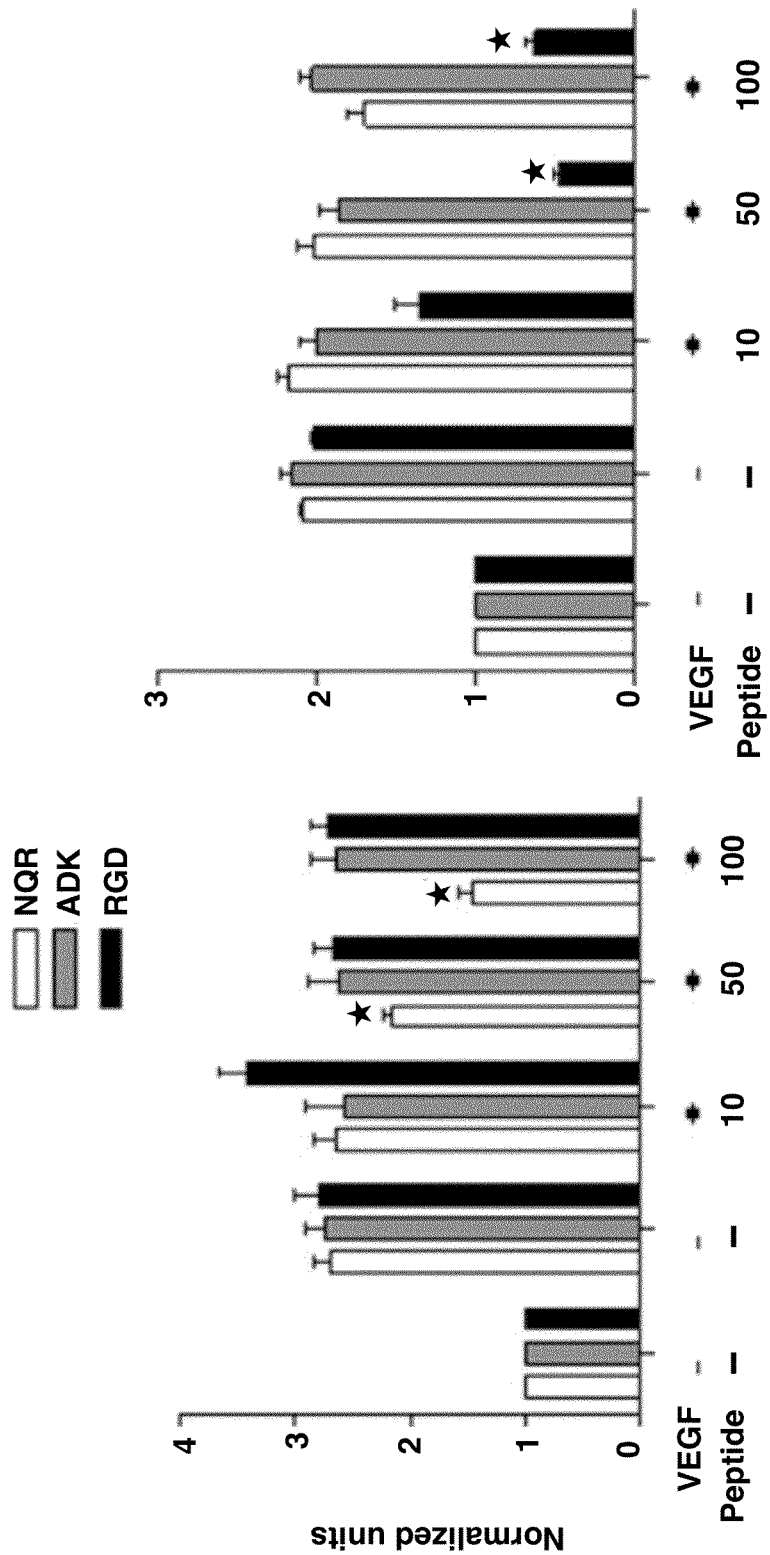

The activities of the NQR, ADK and, RGD peptides were further explored by examining their effect on VEGF-induced signaling events using HUVECs. Distinct profiles of signaling intermediates were found in the ERK1/2 and Akt signaling pathways. The NQR peptide induced a decrease in pERK but had no effect on pAkt, whereas the opposite was observed with the RGD peptide (FIGS. 6A-6B). The ADK peptide had no effect. These results further distinguish the NQR and RGD peptides.

Discussion

The phage peptide display methodology has been used to identify specific peptides that bind differentially to the vascular endothelium of different normal and diseased tissues. However, most previous studies focused on tumors, and there is little information on the vasculature of inflamed joints. The present invention identified three phage-encoded peptides (NQR, ADK, and RGD) that home selectively to an inflamed joint without any significant targeting to normal (uninflamed) tissues. The RGD peptide has been described previously and designated as RGD-4C (15, 20). Apparently NQR and ADK bind to different receptors/receptor domains on the endothelial cell surface than RGD. This inference is supported by three findings: (i) no cross-inhibition of phage binding by these peptides; (ii) inhibition of attachment of HUVECs to vitronectin, which involves integrin αvβ3 integrin, by RGD peptide, but not by NQR or ADK peptide; and (iii) differential alterations in the MAP kinase signaling pathway events induced by NQR peptide versus RGD peptide. The precise identity of the receptors that bind NQR and ADK peptides to vascular endothelial cells remains to be determined.

In terms of functional properties, NQR and RGD, but not ADK, suppressed arthritis. ADK peptide apparently binds to a receptor that does not trigger a detectable tissue response. The antiarthritic activity of NQR is likely attributable, at least in part, to inhibition of angiogenesis and resulting inhibition of leukocyte migration into the inflamed joint. However, one cannot exclude an effect on the survival of the incoming leukocytes. A systemic effect that would reduce leukocyte ingress seems unlikely, given the lack of a known target for the peptide outside the joint.

Although the currently available drugs aimed at limiting inflammation and tissue damage in arthritis are quite potent, their use is associated with significant adverse effects (22). The present invention supports that NQR and ADK peptides can be exploited for therapeutic purposes for delivering drugs with anti-inflammatory, antiangiogenic, or bone damage-protective properties, as well as for delivering imaging molecules or nanoparticles, into inflamed joints (23). The success of a similar approach for antitumor therapy in model systems is elaborated below. By not binding or penetrating the normal tissues, the joint-homing peptides can be a useful arsenal in preventing systemic toxicity and enhancing benefit/risk ratio for antiarthritic compounds conjugated with such peptides. Because these peptides represent randomly generated sequences, there is no inherent bias in their interaction with the target proteins in the joints.

In the case of tumors, which share the process of neoangiogenesis with arthritis, peptides binding to tumor vasculature have been identified and exploited for suppression of tumor growth in model systems (15, 24-27). For example, a peptide coupled to the anticancer drug doxorubicin was found to be a more efficacious anticancer agent compared with the drug alone when tested against human breast cancer tissue implanted as a xenograft in nude mice (15). Similarly, aminopeptidase N (APN, CD13) has been identified as a target for inhibiting angiogenesis and peptides containing an NGR motif have been identified as homing peptides that recognize this enzyme in angiogenic vessels (24).

In the case of arthritis, a peptide (CKSTHDRLC) homing to the human synovial tissue engrafted s.c. in severely combined immunodeficiency mice has been identified (28). However, neither the antiarthritic activity of this peptide nor any mechanistic functional study using that peptide was reported. Furthermore, the anatomic and physiological milieu of the synovial joint can not be fully replicated in grafted synovial tissue. The present study examined in detail the mechanisms underlying the antiarthritic activity of NQR and RGD peptides in the AA model. The NQR sequence also appeared twice in the aforementioned study using human synovium xenografts for phage library screening (28). Another set of studies (7, 8, 29) was based on the interaction between the RGD motif and αvβ3 integrin. For example, fibronectin peptides containing the RGD sequence were shown to inhibit both clinical arthritis and leukocyte recruitment into the joints in rats with streptococcal cell wall-induced arthritis (30). In another study, intra-articular injection of an RGD peptide (RGDfV, SEQ ID NO: 6), which served as an antagonist for αvβ3, was shown to reduce clinical arthritis, synovial angiogenesis, and joint damage in rabbits with antigen-induced arthritis (7). As mentioned earlier, a similar antiarthritic effect of RGDfK peptide was also observed in rats with AA in the present study. However, the RGD motif-bearing peptides bind to integrins that are rather widely distributed in the vasculature of diverse tissues and thus may compromise joint specificity. In addition, an antibody antagonist of αvβ3 showed limited efficacy in a phase II trial in RA patients (5). In this context, the results herein showing that both NQR and ADK differ in their receptor specificity from RGD offer new ligands for further examination of the pathogenesis and treatment of arthritis. Another study found that the RGD-4C-displaying phage homed to inflamed synovium, but not to other tissues of DBA/1 mice with collagen-induced arthritis. Moreover, RGD-4C peptide covalently linked to a proapoptotic heptamer dimer-suppressed arthritis, whereas a simple mixture of the peptide and the heptamer failed to do so (8). In this context, the present invention observed a direct antiarthritic activity of the RGD peptide, as did previous investigators using the rabbit model of arthritis (7). This difference may be related to the different animal model systems used or to differences in experimental conditions. Another group described the suppression of AA after treatment with RGD-displaying liposomes for the delivery of encapsulated dexamethasone phosphate into joints (29). Apoptosis of the hyperplastic synovium in rabbits (31) after the administration of a proapoptotic peptide, $(KLAKLAK)_2$ (SEQ ID NO: 7), fused to a synovial-targeted transduction peptide, HAP-1, also has been reported. Soluble mediators of angiogenesis produced by endothelial cells of inflamed synovium, such as the Ley/H glycoconjugate (32), also represent attractive targets for inhibiting angiogenesis in the treatment of arthritis.

Studies conducted in the K/BXN model of antibody-mediated arthritis have revealed that distal joints of the paws of mice might be particularly vulnerable to arthritis induction due to a vacular leak (4). The transfer of arthritogenic antibodies was found to cause macromolecular vasopermeability at sites prone to developing arthritis. This vasopermeability required mast cells, neutrophils, FcRγIII, histamine, and serotonin, along with some contribution from the gut or the liver. In comparison, these results offer an interesting perspective on target organ selectivity in predominantly T-cell-mediated arthritis, and are distinct from yet complementary to studies describing regional vasopermeability in antibody-mediated arthritis using the K/BXN model (4). NQR and ADK peptide ligands may be used to identify their natural target molecules within the joint tissue. These peptides may uncover new targets that may not have otherwise been implicated in the disease process. Furthermore, a similar approach might pave the way for effective therapeutic approaches for other autoimmune diseases besides arthritis (33-35).

The following references were cited herein:
1. Gorman et al., (2008) Best Pract Res Clin Rheumatol, 22:221-238.
2. Corrigall, V M and Panayi, G S, (2002) Crit Rev Immunol, 22:281-293.
3. David, C S and Taneja, V, (2004) Am J Med Sci 327:180-187.
4. Binstadt, et al. (2006) Nat Immunol 7:284-292.
5. Lainer-Carr, D. and Brahn, E. (2007) Nat Clin Pract Rheumatol, 3:434-442.
6. Szekanecz, Z and Koch, A E (2009) Vascul Pharmacol, 51:1-7.
7. Storgard, et al. (1999) J Clin Invest 103:47-54.
8. Gerlag, et al. (2001) Arthritis Res, 3:357-361.
9. Ruoslahti, E and Rajotte, D (2000) Annu Rev Immunol, 18:813-827.
10. Ruoslahti, E. (2002) Nat Rev Cancer, 2:83-90.
11. Pasqualini, R. and Ruoslahti, E. (1996) Nature 389:364-366.
12. Chen et al., (2009) Nat Med, 15:1215-1218.
13. Whitney, et al. (2011) Nat Biotechnol 29:352-356.
14. Essler, M. and Ruoslahti, E. (2002) Proc Natl Acad Sci USA, 99:2252-2257.
15. Arap, et al. (1998) Science, 279:377-380.
16. Brown, K C (2010) Curr Pharm Des, 16:1040-1054.
17. Askoxylakis, et al. (2010) PLoS ONE, 5:e15962.
18. Gordon, et al., (2010) J Mol Biol, 396:166-177.
19. Deutscher, et al. (2009) J Labelled Comp Radiopharm, 52:583-590.
20. Koivunen, et al. (1994) J Cell Biol, 124:373-380.
21. Sugahara, et al. (2009) Cancer Cell, 16:510-520.
22. Kremers et al. (2004) J Rheumatol, 31:2366-2373.
23. Zhou, et al. (2010) Nanomed, 5:1065-1074.
24. Pasqualini, et al. (2000) Cancer Res, 60:722-727.
25. Chang, et al. (2009) J Biol Chem 284:12905-12916.
26. Matsuo et al. (2010) J Mol Med, 88:1255-1264.
27. Sugahara, et al. (2010) Science, 328:1031-1035.
28. Lee, et al. (2002) Arthritis RheumI 46:2109-2120.
29. Koning, et al. (2006) Arthritis Rheum, 54:1198-1208.
30. Wahl, et al. (1994) J Clin Invest, 94:6555-662.
31. Mi et al., (2003) Mol Ther, 8:295-305.
32. Halloran, et al. (2000) J Immunol, 164:4868-4877.
33. Caturegli, et al. (2007) Curr Opin Rheumatol, 19:44-48.
34. Vasu et al. (2003) Autoimmunity, 36:389-396.
35. van Belle, et al. (2011) Physiol Rev, 91:79-118.
36. Rajaiah, et al. (2011) J Biol Chem, 286:2817-2825.
37. Pasqualini et al. (1995) J Cell Biol, 130:1189-1196.
38. Maeshima et al. (2000) J Biol Chem, 275:23745-23750.

What is claimed is:

1. A peptide that homes to a joint of an animal, comprising a sequence CRNADKFPC (SEQ ID NO. 1).

2. The peptide of claim 1, wherein said peptide has a sequence at least 77% identical to CRNADKFPC (SEQ ID NO. 1).

3. The peptide of claim 1, wherein said peptide has a sequence at least 88% identical to CRNADKFPC (SEQ ID NO. 1).

4. A peptide that homes to a joint of an animal comprising a sequence CLDNQRPKC (SEQ ID NO. 2), comprising a sequence at least 77% identical to CLDNQRPKC (SEQ ID NO. 2) or comprising a sequence at least 88% identical to CLDNQRPKC (SEQ ID NO. 2).

5. A composition, comprising the peptide of claim 4.

6. The composition of claim 5, further comprising a co-composition, wherein the peptide and the co-composition are not covalently coupled or non-covalently associated with each other.

7. The composition of claim 5, wherein the peptide selectively homes to regenerating tissue, a site of injury, a site of inflammation or a site of arthritis.

8. The composition of claim 6, wherein the peptide and the co-composition are chemically conjugated or bound to each other.

9. The composition of claim 6, wherein the co-composition comprises a therapeutic agent, a therapeutic protein, a therapeutic compound, a therapeutic composition, a chemotherapeutic agent, a cancer chemotherapeutic agent, a toxin, a cytotoxic agent, imatinib, an anti-angiogenic agent, an anti-inflammatory agent, an anti-arthritic agent, a TGF-.beta. inhibitor, decorin, a systemic vasodilator, an anti-coagulant, tissue factor pathway inhibitor (TFPI), site-inactivated factor VIIa, a .beta.-2 agonist, salmeterol, formoterol, N-Acetylcysteine (NAC), Superoxide Dismutase (SOD), a superoxide dismutase mimetic, EUK-8, an endothelin (ET-1) receptor antagonist, a prostacyclin derivative, a phosphodiesterase type 5 inhibitor, Ketoconazole, a small interfering RNA (sRNA), a microRNA (miRNA), a polypeptide, a nucleic acid molecule, a small molecule, a carrier, a vehicle, a virus, a phage, a viral particle, a phage particle, a viral capsid, a phage capsid, a virus-like particle, a liposome, bone remodeling agents, tissue regenerating agents, a micelle, a bead, a nanoparticle, a microparticle, a detectable agent, a contrast agent, an imaging agent, a label, a labeling agent, a fluorophore, fluorescein, rhodamine, FAM, a radionuclide, indium-111, technetium-99, carbon-11, carbon-13, a disease-modifying antirheumatic drug, an analgesic or a combination.

10. The composition of claim 9, wherein said anti-angiogenic agent is selected from the group consisting of thrombospondin, angiostatin5, pigment epithelium-drived factor, angiotensin, laminin peptides, fibronectin peptides, plasminogen activator inhibitors, tissue metalloproteinase inhibitors, interferons, interleukin 12, platelet factor 4, IP-10, Gro-.beta., thrombospondin, 2-methoxyoestradiol, proliferin-related protein, carboxiamidotriazole, CM101, Marimastat, pentosan polysulphate, angiopoietin 2 (Regeneron), interferon-alpha, herbimycin A, PNU145156E, 16K Prolactin fragment, Linomide, thalidomide, pentoxifylline, genistein, TNP-470, endostatin, paclitaxel, Docetaxel, polyamines, a proteasome inhibitor, a kinase inhibitor, a signaling peptide, accutin, cidofovir, vincristine, bleomycin, AGM-1470, platelet factor 4 and minocycline.

11. The composition of claim 9, wherein said anti-inflammatory agent is selected from the group consisting of steroids, cortisone, glucocorticoids, prednisone, prednisolone, hydrocortisone (cortisol), cortisone acetate, methylprednisolone, dexamethasone, betamethasone, triamcinolone, beclometasone, and fludrocortisone acetate, non-steroidal anti-inflammatory drug (NSAIDs), ibuprofen, naproxen, meloxicam, etodolac, nabumetone, sulindac, tolementin, choline magnesium salicylate, diclofenac, diflusinal, indomethicin, ketoprofen, oxaprozin, piroxicam, and nimesulide, salicylates, aspirin (acetylsalicylic acid), diflunisal, salsalate, p-amino phenol derivatives, paracetamol, phenacetin, propionic acid derivatives, ibuprofen, naproxen, fenoprofen, ketoprofen, flurbiprofen, oxaprozin, loxoprofen, acetic acid derivatives, indomethacin, sulindac, etodolac, ketorolac, diclofenac, nabumetone, enolic acid (oxicam) derivatives, piroxicam, meloxicam, tenoxicam, droxicam, lornoxicam, isoxicam, fenamic acid derivatives (fenamates), mefenamic acid, meclofenamic acid, flufenamic acid, tolfenamic acid, selective cox-2 inhibitors (coxibs), celecoxib, rofecoxib, valdecoxib, parecoxib, lumiracoxib, etoricoxib, firocoxib, sulphonanilides, nimesulide, and licofelone.

12. The composition of claim 9, wherein said analgesic agent is selected from the group consisting of NSAIDs, COX-2 inhibitors, Celecoxib, Rofecoxib, Valdecoxib, Parecoxib, Lumiracoxib, Etoricoxib, Firocoxib, acetaminophen, opiates, Dextropropoxyphene, Codeine, Tramadol, Anileridine, Pethidine, Hydrocodone, Morphine, Oxycodone, Methadone, Diacetylmorphine, Hydromorphone, Oxymorphone, Levorphanol, Buprenorphine, Fentanyl, Sufentanyl, Etorphine, Carfentanil, dihydromorphine, dihydrocodeine, Thebaine, Papaverine, diproqualone, Flupirtine, Tricyclic antidepressants, and lidocaine.

13. The composition of claim 9, wherein said disease-modifying antirheumatic drug is selected from the group consisting of mycophenolate mofetil (CellCept), calcineurin inhibitors, cyclosporine, sirolimus, everolimus, oral retinoids, azathioprine, fumeric acid esters, D-penicillamine, cyclophosphamide, immunoadsorption column, Prosorba(r) column, a gold salt, auranofin, sodium aurothiomalate (Myocrisin), hydroxychloroquine, chloroquine, leflunomide, methotrexate (MTX), minocycline, sulfasalazine (SSZ), tumor necrosis factor alpha (TNFa) blockers, etanercept (Enbrel), infliximab (Remicade), adalimumab (Humira), certolizumab pegol (Cimzia), golimumab (Simponi)), Interleukin 1 (IL-1) blockers, e.g., anakinra (Kineret), monoclonal antibodies against B cells, rituximab (Rituxan)), T cell costimulation blockers, abatacept (Orencia), Interleukin 6 (IL-6) blockers, tocilizumab, RoActemra, and Actemra.

14. The composition of claim 9, wherein said liposome or said nanoparticle is coated on its surface with the peptide comprising a peptide with a sequence of CLDNQRPKC (SEQ ID NO. 2), comprising a peptide with a sequence at least 77% identical to CLDNQRPKC (SEQ ID NO. 2) or comprising a peptide with a sequence at least 88% identical to CLDNQRPKC (SEQ ID NO. 2).

15. A method of treating a subject having an arthritic joint, comprising the step of administering to said subject a pharmacologically effective dose of the composition of claim 5.

16. A method of treating a subject having an arthritic joint, comprising the step of administering to said subject a pharmacologically effective dose of the composition of claim 9.

17. A method of treating a subject having an arthritic joint, comprising the step of administering to said subject a pharmacologically effective dose of the composition of claim 14.

* * * * *

SEQUENCE LISTING

```
<160> NUMBER OF SEQ ID NOS: 7

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide homing to joint in an animal

<400> SEQUENCE: 1

Cys Arg Asn Ala Asp Lys Phe Pro Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide homing to joint in an animal

<400> SEQUENCE: 2

Cys Leu Asp Asn Gln Arg Pro Lys Cys
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide homing to joint in an animal
<220> FEATURE:
<221> NAME/KEY: MISC_FEATURE
<222> LOCATION: (4)
<223> OTHER INFORMATION: Phe is a D-amino acid
<220> FEATURE:
<221> NAME/KEY: MISC_FEATURE
<223> OTHER INFORMATION: cyclic peptide

<400> SEQUENCE: 3

Arg Gly Asp Phe Lys
1               5
```

```
<210> SEQ ID NO 4
<211> LENGTH: 9
<212> TYPE: PRT
<213> ORGANISM: Artificial Sequence
<220> FEATURE:
<223> OTHER INFORMATION: Synthetic peptide homing to a joint in an
      animal
<220> FEATURE:
<221> NAME/KEY: MISC_FEATURE
<223> OTHER INFORMATION: cyclic peptide

<400> SEQUENCE: 4

Cys Asp Cys Arg Gly Asp Cys Phe Cys
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide homing to a joint in an
      animal

<400> SEQUENCE: 5

Cys Lys Ser Thr His Asp Arg Leu Cys
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide homing to a joint in an
      animal
<220> FEATURE:
<221> NAME/KEY: MISC_FEATURE
<222> LOCATION: (4)
<223> OTHER INFORMATION: Phe is a D-amino acid
<220> FEATURE:
<221> NAME/KEY: MISC_FEATURE
<223> OTHER INFORMATION: cyclic peptide

<400> SEQUENCE: 6

Arg Gly Asp Phe Val
1               5

<210> SEQ ID NO 7
<211> LENGTH: 14
<212> TYPE: PRT
<213> ORGANISM: Artificial Sequence
<220> FEATURE:
<223> OTHER INFORMATION: synthetic proapoptotic dipeptide

<400> SEQUENCE: 7

Lys Leu Ala Lys Leu Ala Lys Lys Leu Ala Lys Leu Ala Lys
1               5                   10
```